(12) United States Patent
Blau et al.

(10) Patent No.: US 10,188,463 B2
(45) Date of Patent: Jan. 29, 2019

(54) BONE LENGTH DETERMINATION

(71) Applicant: STRYKER TRAUMA GMBH, Schönkirchen / Kiel (DE)

(72) Inventors: Arno Blau, Staufen im Breisgau (DE); Bernd Simon, Kiel (DE); Lars Metz, Kiel (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 217 days.

(21) Appl. No.: 15/119,035

(22) PCT Filed: Feb. 18, 2014

(86) PCT No.: PCT/EP2014/053136
§ 371 (c)(1),
(2) Date: Aug. 15, 2016

(87) PCT Pub. No.: WO2015/124171
PCT Pub. Date: Aug. 27, 2015

(65) Prior Publication Data
US 2016/0354156 A1  Dec. 8, 2016

(51) Int. Cl.
*A61B 34/10* (2016.01)
*A61B 6/00* (2006.01)
*A61B 17/17* (2006.01)
*A61B 90/00* (2016.01)

(52) U.S. Cl.
CPC ............ *A61B 34/10* (2016.02); *A61B 6/4441* (2013.01); *A61B 6/487* (2013.01); *A61B 6/505* (2013.01); *A61B 6/5217* (2013.01); *A61B 17/1703* (2013.01); *A61B 17/1725* (2013.01); *A61B 2034/108* (2016.02); *A61B 2090/3966* (2016.02)

(58) Field of Classification Search
CPC ..... A61B 34/10; A61B 17/17; A61B 17/1703; A61B 17/1725; A61B 6/487; A61B 6/505; A61B 6/5217; A61B 6/4441
See application file for complete search history.

(56) References Cited

U.S. PATENT DOCUMENTS

| 2011/0082367 A1 | 4/2011 | Regazzoni |
| 2013/0317512 A1 | 11/2013 | Buhren et al. |
| 2013/0322726 A1 | 12/2013 | Nathaniel |

FOREIGN PATENT DOCUMENTS

| EP | 2363083 A1 | 9/2011 |
| WO | 2014048447 A1 | 4/2014 |

OTHER PUBLICATIONS

International Search Report for Application No. PCT/EP2014/053136 dated Nov. 25, 2014.

(Continued)

*Primary Examiner* — Christopher Beccia
(74) *Attorney, Agent, or Firm* — Lerner, David, Littenberg, Krumholz & Mentlik, LLP

(57) ABSTRACT

A method and a device are provided, for measuring an actual length of a fractured bone based on 2D fluoroscopic images of proximal and distal sections of the bone, each of the images including a reference body. Based on the images, a spatial position of a first end point and a spatial position of a second end point are determined, taking into account dimensions taken from a bone model of a bone corresponding to the imaged bone and the spatial positions of the reference bodies. The actual length of the fractured bone is defined as the distance between the two end points.

20 Claims, 4 Drawing Sheets

(56) References Cited

OTHER PUBLICATIONS

Schulz, A.P. et al., "Evidence Based Development of a Novel Lateral Fibula Plate (VariAx Fibula) Using a Real CT Bone Data Based Optimization Process During Device Development," The Open Orthopaedics Journal, 2012, 6, 1-7.

BONE LENGTH DETERMINATION

CROSS-REFERENCE TO RELATED PATENT APPLICATION

The present application is a national phase entry under 35 U.S.C. § 371 of International Application No. PCT/EP2014/053136, filed Feb. 18, 2014, published in English, incorporated herein by reference.

FIELD OF THE INVENTION

The invention relates to the field of computer assisted surgery. In particular, the invention relates to a method and a device for determining an actual length of a fractured bone based on fluoroscopic images. The method may be implemented as a computer program executable on a processing unit of the device.

BACKGROUND OF THE INVENTION

In a case in which a shaft of a long bone is fractured, a bone nail may be used to stabilize the parts of the bone during the healing of the fracture, wherein the bone nail may be inserted into a medullary channel of the bone in a longitudinal direction thereof. However, such a bone nail may allow a shifting of one part of the bone relative to another part of the bone, along the axis of the bone nail, at least until a locking screw is inserted through the bone nail in a lateral direction to fix the position of the shiftable part.

Accordingly, a physician should position the fractured parts as anatomically correct as possible. One approach may be to take into account features of the healthy counterpart of the fractures bone to provide information regarding how the parts of the fractured bone should be arranged. But this is difficult, since the bone of the counterpart is usually not visible.

SUMMARY OF THE INVENTION

It may be seen as an object of the invention to provide a method and a device for assisting a determination of an actual distance of a first feature of a first bone section relative to a second feature of a second bone section, with only one of the bone sections being visible in a respective fluoroscopic image. This is achieved by the subject-matter of each of the independent claims. Further embodiments are described in the respective dependent claims.

According to a first aspect of the invention, a method is provided, for measuring an actual length of a fractured bone, wherein an implant is already introduced into the fractured bone, with a first reference body and a second reference body being already arranged in a predetermined relation to the fractured bone and implant.

Firstly, a first 2D fluoroscopic image is received, the first image including the first reference body and a first bone feature, wherein the first bone feature defines a first end of the bone, and a second 2D fluoroscopic image is received, the second image including the second reference body and a second bone feature, wherein the second bone feature defines a second end of the bone, wherein at least one of the ends is not visible in the respective fluoroscopic image. Based on the received images, a first spatial relation between the first reference body and the first end, and a second spatial relation between the second reference body and a visible aspect of the second bone feature is determined. Then, data of a bone model with corresponding first and second bone features are received and a third spatial relation between the visible aspect of for example the second bone feature and a second end of the bone is determined at the bone model. Finally, an actual length of the bone is determined based on the first, second, and third spatial relation, and on the predetermined relation of the reference bodies to each other.

According to an embodiment, the first spatial relation between the first reference body and the first end of the bone may be determined by determining a fourth spatial relation between the first reference body and another visible aspect, i.e. a second point of the first bone feature, and determining a fifth spatial relation between the visible aspect of the first bone feature and the first end point based on or at the bone model.

According to an embodiment, at least one of the first and second 2D fluoroscopic images may be generated in a direction being perpendicular to an axis of a bone shaft. On the other hand, at least one of the first and second 2D fluoroscopic images may be generated in a direction being inclined to an axis of a bone shaft.

It is noted that the data of the fluoroscopic images may be received directly from an imaging device, for example from a 2D C-arm based X-ray device, or alternatively from a data base. The image may represent an anatomical structure of interest, in particular a bone.

Any bone, for example a bone at a hand or foot, in particular a long bone of the lower extremities, like the femur and the tibia, and of the upper extremities, like the humerus, may be subject to an embodiment of the method. That is, a distance between a feature at for example the proximal section of a respective bone and a feature at the distal section of the respective bone may be determined. It is noted that such a determination of a feature may be performed based on gray scale image data which may be received for example from an x-ray imaging unit.

As used herein, the term "feature of a bone" refers to anything at a bone which may be suitable for determining a geometrical aspect, i.e. a point, a line, an arc, a center point, an axis, a cylinder surface, a ball surface, or the like, wherein such geometrical aspects are in particular suitable for a determination of a longitudinal axis and/or a vector. For example, a geometrical aspect of a femur may be the outer surface of the femur head, an axis defined by the neck between shaft and femur head, a longitudinal axis of the femur shaft, a most distal point on the bone surface, a line defined by the center points of the condyles, or a line defined by the most posterior points at the condyles. It will be understood that the other long bones provide other and/or comparable geometrical aspects.

As used herein, the term "feature of a bone" may also encompass any feature of an implant being already inserted into a bone or at least fixedly connected to a bone, said feature being suitable for determining a geometrical aspect as mentioned above.

According to another embodiment, at least one of the feature of the first bone section and the feature of the second bone section is determined on the basis of a 2D image of at least a section of the bone, wherein the 2D image further includes a visualization of a reference body. The reference body may comprise a structure forming a characteristic 2D projection image for determining a 3D orientation of the reference body. In other words, based on one 2D projection image, a 3D orientation of the reference body can be determined, leading to a determination of a 3D orientation of a feature of a bone.

The reference body may be adapted to be fixedly connected to the bone. As used herein, each of the terms "fixedly connected", "fixedly coupled" and "fixedly attached" encompasses a direct or an indirect connection of an element to another element. For example, a reference body may be directly attached at an implant or may be indirectly coupled to an implant, with for example an aiming device between the reference body and the implant. On the other hand, a reference body which is integrated into an implant, i.e. which can be considered as fixedly connected to the implant, may be considered as being indirectly coupled to a bone, i.e. via the implant.

As a first example, the reference body may be integrated into a leading end of a bone nail so that when a trailing end of the bone nail is already fixed to a first section of the bone, the reference body may be located within the second section of the bone and may thus be visible in an image of that second section.

As a second example, the reference body may be integrated into an aiming device for supporting an insertion of a locking screw through a bore in a leading end of a bone nail. Therefore, the aiming device may be adapted to be coupled to a trailing end of the bone nail and may extend outside the body of a patient as far as the bone nail extends inside the bone so that at least a portion of the aiming device can be visible in an image of the second section of the bone including the leading end of the bone nail.

As use herein, the term "bone model" encompasses, for example, a 3D model of a bone. The bone model may be generated based on at least one 3D scan of at least one real bone of the same kind, for example a femur or humerus, and/or by forming an average from a plurality of 3D scans. An exemplary utilization of bone models is described in 'Evidence based development of a novel lateral fibula plate (VariAX Fibula) using a real CT bone data based optimization process during device development' of A. P. Schulz et al. (The Open Orthopaedics Journal, 2012, 6, 1-7), the content of which is incorporated herein by reference.

According to a further embodiment, the method may further comprise the step of determining a diameter of the imaged bone between two opposed outer surfaces of the imaged bone in relation to a reference body which is also visible in the X-ray image. The diameter may be the distance between both outer bone surfaces in a transverse direction of the bone.

It is noted that the dimensions of the reference body is known so that a factor can be calculated representing the relation between, for example, a length of the reference body as imaged and an actual length of the reference body. This factor may subsequently be used to determine for example an actual diameter of an imaged bone. The actual diameter of the imaged bone may in turn lead to a bone model, wherein at least the size of the bone model fits to the imaged bone so that a length or distance which is not visible in the image can be determined at the bone model.

A particular bone like a femur has an almost constant relation between its length and its width, i.e. the femur has a specific shape regardless of its size. Therefore, a bone model can be selected based on only one measured dimension, for example a diameter of the shaft in one direction. It can be assumed as very likely that other dimensions of the bone model like the length or a diameter perpendicular to the measure diameter correlate to the corresponding actual dimensions of an imaged bone.

According to another embodiment, the method further comprises the step of selecting a bone model from a group of bone models with different sizes and shapes, the selected bone model corresponding to the imaged bone. The group of bone models may be stored in a database. Further, the group of bone models may be a selection of previously generated 3D images, each of another person, wherein the persons may differ in size, weight and age. The database may thus contain several models of each bone (e.g. tibia, femur, humerus) including bone models of different ages, genders and individual sizes. The software uses gray scale image data to determine at least one dimension from the x-ray (2D image) of the bone to be treated and searches the database for a bone model of a person of the same age, gender and size, for example, having an identical or at least a close approximation to the at least one dimension from the bone to be treated. When a match is determined a three dimensional model of the matched bone in the database is selected and utilized as a corresponding 3D bone model of the bone to be treated.

According to yet another embodiment, the method further comprises the step of adapting a bone model so that the bone model corresponds to the imaged bone. Also here, the bone model may be stored in a database. In this case, the bone model may be generated by forming an average of a plurality of previously generated 3D images. To adapt the bone model to the imaged bone, substantially the size of the bone model may be increased or decreased so as to fit to the size of the bone as measured in the image, with shape relations being constant.

An improved result may be achieved based on a second X-ray image generated from a second imaging direction. Accordingly, the method may further comprises the step of determining a diameter of the imaged bone between two opposed outer surfaces of the imaged bone in relation to the reference body which is also visible in a second X-ray image of the bone, wherein the imaging directions of the first X-ray image and the second X-ray image differ from each other.

Although the shape of one bone, for example a femur, does usually not vary with an increasing size, at least as a first approximation, sometimes the shape may not be as expected. Therefore, a second X-ray image may serve as a means to control the expected dimensions of an imaged bone to ensure that the used bone model fits both in size and shape to the imaged bone.

According to an embodiment, the method does not comprise any step of inserting an implant into a bone and/or connecting a reference body at the implant and thus at the bone, in so far as it constitutes a treatment of a human or animal body by surgery.

According to a second aspect of the invention, a device is provided for measuring an actual length of a fractured bone, wherein a first reference body and a second reference body are arranged in a predetermined relation to the implant. Generally, the device comprises a receiving unit and a processing unit. The receiving unit may receive (i) a first 2D fluoroscopic image including the first reference body and a first bone feature, the first bone feature defining a first end of the bone, (ii) a second 2D fluoroscopic image including the second reference body and a second bone feature, the second bone feature defining a second end of the bone, wherein the second end may be not visible in the second fluoroscopic image, and (iii) data of a bone model having first and second bone features corresponding to the first and second bone features of the bone. The processing unit may determine (i) a first spatial relation between the first reference body and the first end, (ii) a second spatial relation between the second reference body and a visible aspect of the second bone feature, (iii) a third spatial relation between the visible aspect of the second bone feature and the second end at the bone model, and (iv) the actual length of the bone based on the first, second, and third spatial relation, and on the predetermined relation of the reference bodies to each other and to the bone.

It is noted, that the processing unit may be realized by only one processor performing all the steps of the method, or by a group or plurality of processors, for example a system processor for processing the image data including an identification of anatomical structures like a bone surface, a separate processor specialized on a determination of geometrical aspects or on processing of a bone model and determining distances, and a further processor for controlling a monitor for visualizing the result.

According to an embodiment, the device may further comprise at least two reference bodies including an arrangement of elements which allows a reconstruction of a 3D orientation of the reference body based on a 2D projection image. The processing unit of the device may further be adapted for identifying a projection of a reference body in a projection image and for determining a 3D orientation of the reference body.

According to an embodiment, the device further comprises an aiming device, wherein a first and a second reference body are part of the aiming device, i.e. are integrated in or attached to the aiming device.

According to an embodiment, the device comprises storage means providing a database for storing, for example, at least one bone model. It will be understood, that such storage means may also be provided in a network to which the system may be connected and information related to the bone model, i.e. different types of models and parameter thereof, may be received over that network.

Furthermore, the device may comprise an imaging unit for generating the at least one 2D fluoroscopic image, wherein the imaging unit may be capable of generating images from different directions. Accordingly, the imaging unit of the device may be adapted to also provide 3D image data of at least a section of the bone.

The device may further comprise input means for manually determining a position in the fluoroscopic image, for example a bone surface, for measuring a distance in the image. Such input means may be for example a computer keyboard, a computer mouse or a touch screen, to control a pointing device like a cursor on a monitor screen which may also be included in the device.

According to yet another embodiment, the processing unit is further adapted for adapting the bone model so that the shape and size of the bone model correspond to the shape and size of the imaged bone.

According to a further embodiment, a computer software is provided including sets of instructions which when executed on an appropriate device, causes the device to perform the steps of the method as described above.

The computer software may include sets of instructions for determining a position on a bone surface and/or a diameter between outer surfaces so that such determination may be performed automatically. It will be understood that the computer program may further include sets of instructions to identify a reference object in the image.

A corresponding computer program may preferably be loaded into a work memory of a data processor. The data processor or processing unit may thus be equipped to carry out at least a part of the described method. Further, the invention relates to a computer-readable medium such as a CD-ROM at which the computer program may be stored. However, the computer program may also be presented over a network like the World Wide Web and can be downloaded into the working memory of the data processor from such a network.

It has to be noted that embodiments are described with reference to different subject-matters. In particular, some embodiments are described with reference to method type claims (computer program) whereas other embodiments are described with reference to apparatus type claims (device). However, a person skilled in the art will gather from the above and the following description that unless other notified in addition to any combination of features belonging to one type of subject-matter also any combination between features relating to different subject-matters is considered to be disclosed with this application.

The aspects defined above and further aspects, features and advantages of the present invention can also be derived from the examples of the embodiments to be described hereinafter and are explained with reference to examples of embodiments also shown in the figures, but to which the invention is not limited.

Figure 1:
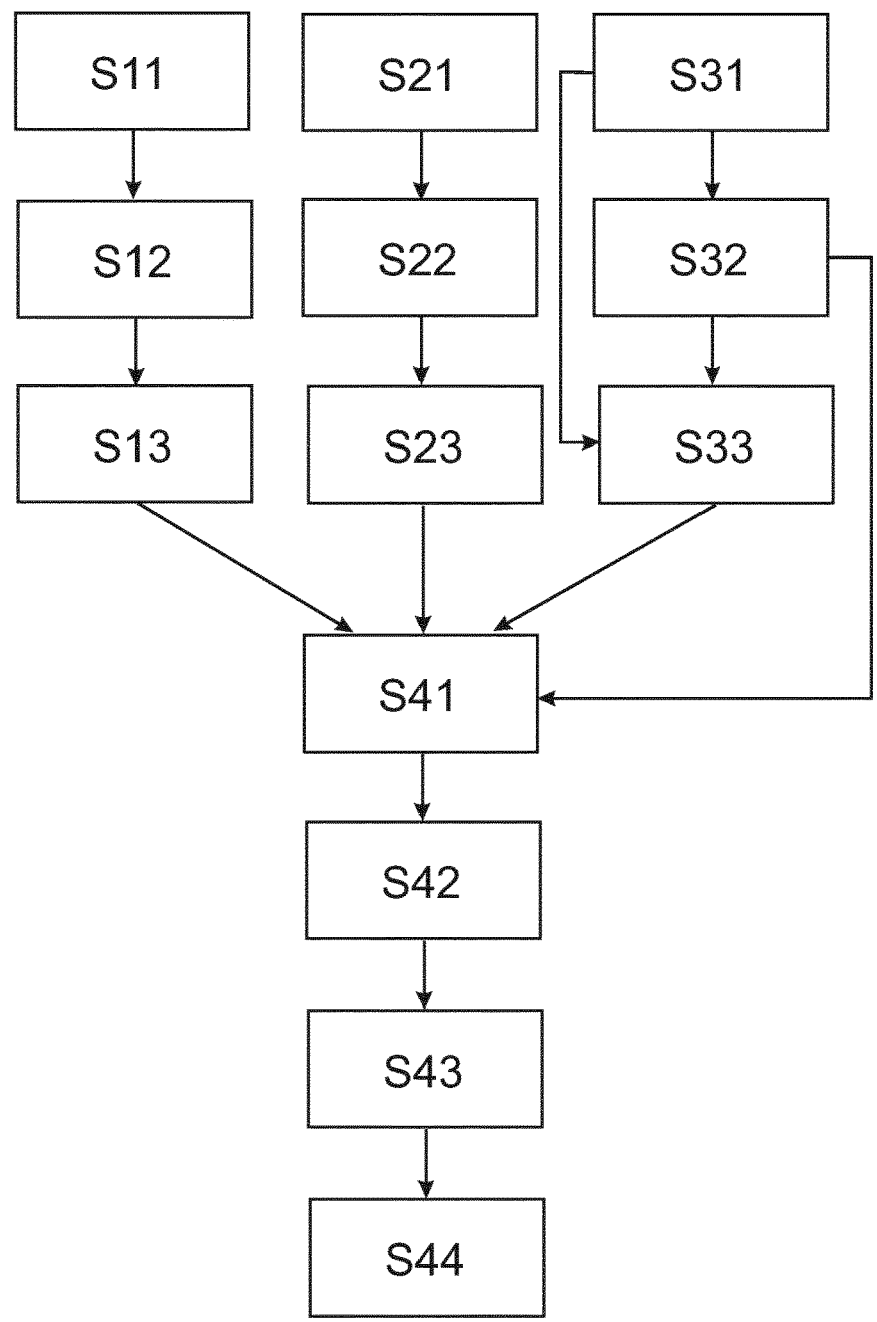
FIG. 1 shows a flow chart of steps of an embodiment of a method.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures.

DETAILED DESCRIPTION OF THE EMBODIMENTS

The flow-chart in FIG. 1 illustrates the principle of the steps performed in accordance with one embodiment of the disclosed method. It will be understood that the steps described, are major steps, wherein these major steps might be differentiated or divided into several sub-steps. Furthermore, there might be also sub-steps between these major steps.

In accordance with one method, in step S11, a first image of a bone is received. The first image may be a fluoroscopic image of a proximal section of a long bone. For example, the image may be generated in a lateral to medial direction, i.e. substantially perpendicular to a longitudinal axis of the long bone. In step S12, a visible aspect or feature of the bone as well as elements of a first reference body 66 are detected in the received image. In step S13, a spatial position of a first point C, T at the bone is determined ($\Delta L4$ or $\Delta L4'$ in FIG. 3).

In step S21, a second image of the bone is received. The second image may also be a fluoroscopic image, but of a distal section of the bone. That second image may particularly be generated inclined with an angle $\alpha$ relative to the longitudinal axis of the bone. In step S22, a visible aspect or feature of the bone as well as elements 64 defining a second reference body are detected in the second image. In step S23, a spatial position of a second point P at the bone is determined.

As used herein, the term "receiving an image" basically refers to the fact that at least one image is necessary to perform the subsequent steps. That is, the term "receiving an image" may encompass both a receiving of an image directly when generated by an imaging device, and a loading of an image from a data base into a processing unit. It is just required that a received image is suitable to identify an aspect or feature of a bone and additionally a reference body (in case of a 2D image).

It is noted that a basic aspect of the determination of a spatial position of a point based on a 2D image is the determination of the spatial position and orientation of the reference body, based on the specific projection of the reference body as shown in the image, so that the reference body defines a 3D coordinate system with a known root in space. Furthermore, the reference body provides a scaling factor in the image, as the actual distances between the elements of the reference body are known and the projected distances can be measured. In relation to such a 3D coordinate system, it is possible to determine a spatial relation between the reference body and a detected aspect or feature at a bone. In other words, it is possible to determine a point within the 3D coordinate system defined by the reference body.

Figure 3:
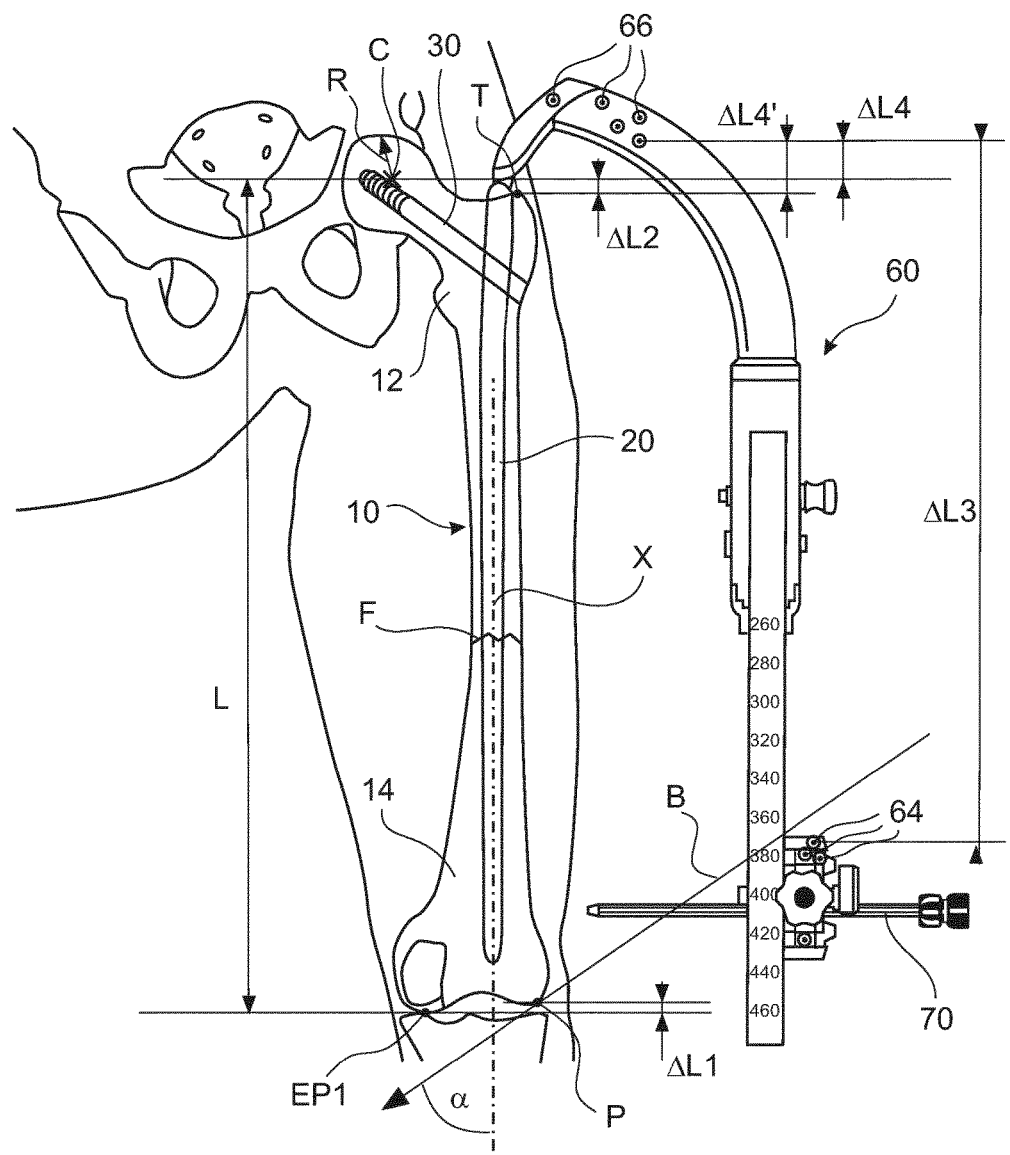
FIG. 3 shows an exemplary illustration of a femur in an anterior to posterior direction.

For example, a distance between one of the elements of the proximal reference body 66 and an anatomical point like the greater trochanter T can be measured in a 2D-image (see FIG. 3). The actual distance $\Delta L4'$ can be calculated as the measured distances multiplied by the scaling factor of the reference body.

In step S31, a dimension like the diameter of the shaft of the bone is determined in either the first and/or the second image. As next step, either a specific bone model of a bone corresponding to the imaged bone is selected in step S32, the size of which fits to the imaged bone, or a general bone model of a bone corresponding to the imaged bone is taken in step S33 and the size of it is adapted by scaling the dimensions so that the model fit to the bone with the determined dimension. It will be understood that it may also be possible to select a bone model the size and shape of which approximately fits to the imaged bone, and then adapt the selected model so as to better fit to the imaged bone.

In step 41, for the case that one of the points determined at the bone is not the end point of the bone, said point at the bone is transferred onto the bone model. It is noted that a tangent point may be transferred, as the angle $\alpha$ of the tangent relative to the longitudinal axis of the bone can be determined on the basis of the reference body visible in the 2D-image. In step S42, an end point of the bone is determined at the bone model starting from the determined point. In step S43, if necessary, an end point of the bone at the opposite end is determined at the bone model starting from the other point at the bone. Finally, the actual length of the fractured bone is determined in step S44, based on the proximal and distal end points taking into account the known distance between the first and second reference bodies, i.e. the distance between the root points of the coordinate systems defined by the reference bodies.

It should be noted that these method steps may be performed to determine a length of a healthy bone, and may also be performed to check whether the length of a fractured bone is anatomically correctly in comparison with the healthy counterpart.

Figure 2:
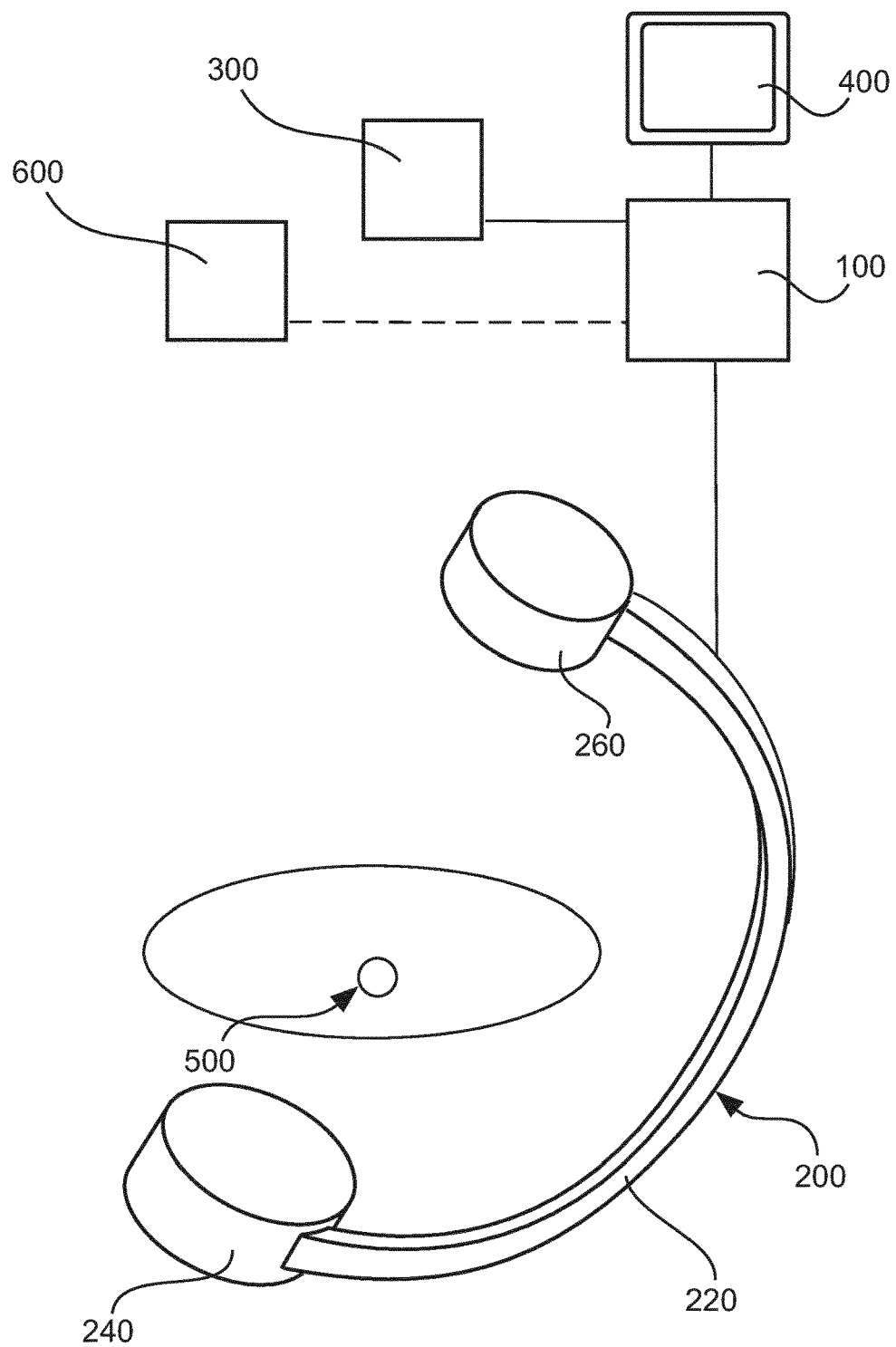
FIG. 2 shows a schematical illustration of a system.

FIG. 2 shows an exemplary embodiment of a device. Substantially, necessary for performing the described steps, a processing unit 100 together with a monitor 400 is part of the device.

An exemplary imaging device 200 includes an X-ray source 240, and an X-ray detector 260, wherein these two devices are mounted on a C-arm 220. It will be understood that the device may also comprise a non-invasive imaging modality like a computer tomography device, a magnetic resonance device, or an ultrasound device as imaging device instead of or additional to the shown C-arm based X-ray device.

Furthermore, the system in FIG. 2 includes an input device 300, by means of which for example a manual determination of a bone feature may be performed. Also shown is a connection (as dotted line) to a database 600, located for example in a network.

Finally, there is shown a region of interest 500. Within said region, for example a bone of a patient may be located which is subject to the method.

Figure 4:
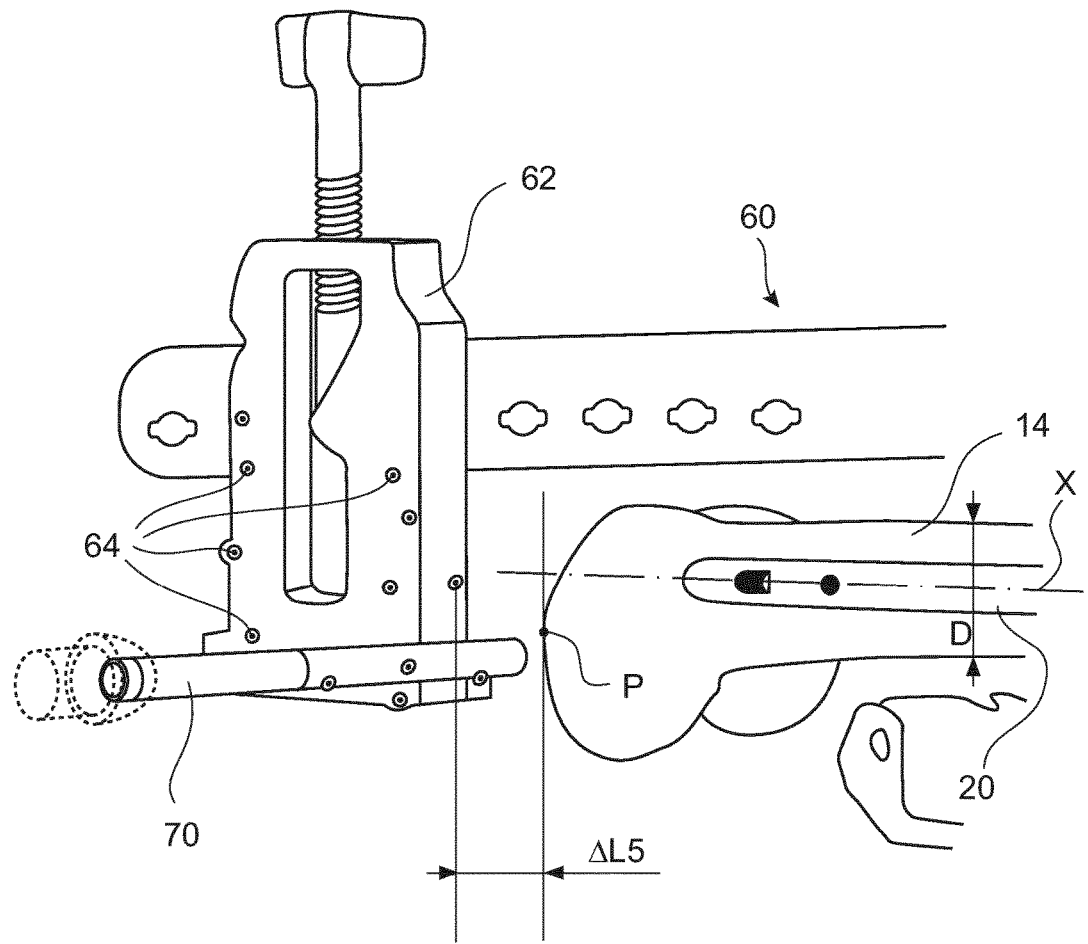
FIG. 4 shows a visualization of a distal section of a femur generated in a lateral and inclined direction.

FIGS. 3 and 4 show schematically illustrations of exemplary images which may form a basis for performing the method. In this example, a length L between a predetermined point at a first section 12, i.e. a proximal section, and a predetermined point at a second section 14, i.e. a distal section of a bone, i.e. a femur 10 is determined, with a fracture F in the shaft of the femur 10. Due to the fracture, the first section 12 may be shifted in a longitudinal direction relative to the second section 14, so that the length L may vary.

FIG. 3 is an image generated in an anterior to posterior direction, i.e. from above (assuming that the patient is lying on his/her back). FIG. 3 shows a situation in which a bone nail 20 is already inserted into a medullary channel of the femur 10 in a longitudinal direction of the femur. Furthermore, the proximal section 12 of the femur 10 is fixed relative to the bone nail 20 by means of a locking screw 30, for example a femoral neck screw, inserted through a bore in the bone nail and into the head of the femur. Fixedly attached to the bone nail 20 is an aiming device 60 with a sleeve 70 for an insertion of a further locking screw to be inserted in the distal section 14 of the femur.

The aiming device 60 comprises a proximal reference body 66 and a distal reference body 64. As shown in FIG. 3 as well as in FIG. 4, each reference body is formed by a plurality of elements. Each of these elements 64, 66 may be a small radiopaque sphere so that each element may be shown as a point in a fluoroscopic image. Due to a specific 3D distribution of the elements 64, 66 at or within the adjusting device 62, a projection of the elements onto an imaging plane will lead to a unique 2D distribution so that an actual 3D orientation of the reference body can be determined based on the projected 2D distribution. Knowing the actual 3D orientation of the reference body allows the determination of a spatial position of a point in the image.

The proximal reference body is arranged at or within the aiming device so that the reference body 66 will be located adjacent the proximal end of the bone. In a fluoroscopic image of the proximal section 12 of the bone, both the section 12 and the reference body can be visible, so that a spatial relation of a point at the bone section to a point at the reference body can be determined.

It is noted that any suitable point at the bone and at the reference body may be used. For example, the most proximal point at the greater trochanter T or the center point of the femur head C may be determined at the bone. On the other hand, any center of one of the spheres which form the reference body 66 may be determined, or a center of gravity of all spheres may also be determined.

Keeping in mind that it is possible to determine a 3D position and orientation of the reference body based on a single 2D projection image of the reference body, and that the distances between and the orientations relative to each other of the spheres of the reference body are known, a spatial position of a point at the bone relative to a spatial position of a point at the reference body can be determined, i.e. a 3D vector between these points.

Consequently, a spatial position of a point P at the distal section 14 of the bone can be determined based on one fluoroscopic image of the distal section 14, the image including the reference body 64. FIG. 4 shows an example of such an image of the distal section. As can be seen in FIG. 4, the fluoroscopic image may be generated from a lateral direction but also inclined in a proximal to distal direction.

It is noted that the distribution of the spheres of a reference body in a projection image allows a determination of an imaging angle $\alpha$ between the viewing direction (arrow B in FIG. 3) and a longitudinal axis X of the bone.

That is, from a fluoroscopic image as visualized in FIG. 4, firstly a point P of a vertical tangent line at the side of the condyles, secondly a distance $\Delta L5$ between said point P and an element of the reference body 64, and thirdly an angle $\alpha$ can be determined.

Additionally shown in the image of FIG. 4, is an aiming device 60 including an adjusting element 62 for adjusting a height for inserting a locking screw through a bore in the leading end of a bone nail 20, and a sleeve 70 for facilitating the insertion of a locking screw.

From a data base of femurs it may be known that dimensions at a femur have usually specific relations (with minor deviations), for example the width of the shaft or the diameter of the femur head relative to the length. Therefore, a distance $\Delta L1$ in a longitudinal direction between a most distal end point EP1 at the condyles and a point P at the side of a condyle may be estimated, for example, based on a measured width D of the femur shaft, taking the relations of the dimensions from the data base of femurs. It will be understood that such estimation may also be done for other bones.

Finally, an actual length of a bone can be determined based on the knowledge of the distance $\Delta L3$ between the first and second reference bodies 64, 66, and on the determined spatial relations of a first point T, C at the proximal end section of the bone relative to the proximal reference body 66 ($\Delta L4$ or $\Delta L4'$) as well as the determined spatial relations of a second point P at the distal end section of the bone relative to the distal reference body 64 ($\Delta L1$), taking into account information related to dimensions of a respective bone from a data base.

While embodiments has been illustrated and described in detail in the drawings and afore-going description, such illustrations and descriptions are to be considered illustrative or exemplary and not restrictive, the invention is not limited to the disclosed embodiments.

Other variations to the disclosed embodiments can be understood and effected by those skilled in the art in practising the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims.

The mere fact that certain measures are recited and mutually different dependent claims does not indicate that a combination of these measures can not be used to advantage. The computer program may be stored/distributed on a suitable medium such as an optical storage medium or a solid-state medium supplied together with or as a part of another hardware, but may also be distributed in other forms, such as via the Internet or other wired or wireless telecommunication systems. Any reference signs in the claims should not be construed as limiting the scope.

LIST OF REFERENCE SIGNS 10 bone/femur
12 first/proximal section of bone/femur
14 second/distal section of bone/femur
20 bone nail
30 locking screw
60 aiming device
62 adjusting device
64, 66 elements of reference body
70 sleeve
100 processing means
200 imaging device
220 C-arm
240 X-ray source
260 X-ray detector
300 input device
400 monitor
500 region of interest
600 database
$\alpha$ angle
B viewing direction
C Center of femur head
D diameter of bone shaft
EP1 distal end point
F fracture
L length
$\Delta L1$, $\Delta L2$ distance
P point
R radius
X longitudinal axis

The invention claimed is:

1. A method for measuring an actual length of a fractured bone, wherein an implant is already introduced into the fractured bone, wherein a first reference body and a second reference body are already arranged in a predetermined relation to the implant, the method comprising the steps of:

receiving a first 2D fluoroscopic image including the first reference body and a first bone feature;

determining a first spatial relation between the first reference body and a first end point at the first bone feature;

receiving a second 2D fluoroscopic image including the second reference body and a second bone feature;

determining a second spatial relation between the second reference body and a second point (P) at the second bone feature;

receiving data of a bone model having corresponding first and second bone features, determining a third spatial relation between the second point (P) of the second bone feature and a second end point (EP1) at the bone model; and determining the actual length of the fractured bone based on the first, second, and third spatial relation, and on the predetermined relation of the reference bodies to each other.

2. The method of claim 1, wherein the first spatial relation between the first reference body and the first end point of the bone is determined by:
  determining a fourth spatial relation between the first reference body and a visible aspect (T) of the first bone feature and
  determining a fifth spatial relation between the visible aspect (T) of the first bone feature and the first end at the bone model.

3. The method of claim 1, wherein at least one of the first and second 2D fluoroscopic images is generated in a direction being perpendicular to an axis of a bone shaft.

4. The method of claim 1, wherein at least one of the first and second 2D fluoroscopic images is generated in a direction being inclined to an axis of a bone shaft.

5. The method of claim 1, wherein the reference body comprises a structure forming a characteristic 2D projection image for determining a 3D orientation of the reference body.

6. The method of claim 1, further comprising the step of selecting a specific bone model from a group of bone models with different sizes and shapes, with the selected bone model corresponding to the imaged bone.

7. The method of claim 1, further comprising the step of adapting a general bone model so that the bone model corresponds to the imaged bone.

8. A device for measuring an actual length of a fractured bone into which an implant is introduced, wherein a first reference body and a second reference body are arranged in a predetermined relation to the implant, the device comprising:
  a receiving unit for receiving a first 2D fluoroscopic image including the first reference body and a first bone feature of the fractured bone, the first bone feature defining a first end point of the bone, receiving a second 2D fluoroscopic image including the second reference body and a second bone feature of the fractured bone, the second bone feature defining a second end point of the bone, with the second end point being not visible in the second 2D fluoroscopic image, and receiving data of a bone model having first and second bone features corresponding to the first and second bone features of the imaged bone; and
  a processing unit for determining a first spatial relation between the first reference body and the first end point, determining a second spatial relation between the second reference body and a second point at the second bone feature, determining a third spatial relation between the second point at the second bone feature and the second end point based on the bone model, and determining the actual length of the fractured bone based on the first, second, and third spatial relation, and on the predetermined relation of the reference bodies to each other.

9. The device of claim 8, further comprising a database for storing at least one bone model.

10. The device of claim 8, wherein the processing unit is further adapted for adapting the bone model so that the shape and size of the bone model correspond to the shape and size of the imaged bone.

11. The device of claim 8, wherein the first and second reference bodies are part of an aiming device.

12. The device of claim 8, further comprising an imaging unit for generating 2D fluoroscopic images.

13. The device of claim 8, wherein the processing unit is further adapted for identifying a projection of a reference body and for determining a 3D position and orientation of the reference body.

14. A computer software which when executed on the processing unit of the device of claim 8, causes the device to perform the steps of the method of claim 1.

15. A method for measuring an actual length of a fractured bone comprising:
  implanting an implant into the fractured bone;
  coupling a first radio-visible reference body and a second radio-visible reference body to the implant in a predetermined relationship to the implant;
  receiving a first 2D fluoroscopic image including the first reference body and a first bone feature of the fractured bone;
  determining a first spatial relationship between the first radio-visible reference body and a first end point on the first bone feature;
  receiving a second 2D fluoroscopic image including the second radio-visible reference body and a second bone feature of the fractured bone, but not the first bone feature of the fractured bone;
  determining a second spatial relationship between the second reference body and a second point on the second bone feature;
  receiving data of a bone model having first and second bone features corresponding to the first and second bone features of the fractured bone;
  determining a third spatial relationship between the second point of the second bone feature and a second end point of the bone model; and
  determining the actual length of the fractured bone based on the first, second, and third spatial relationships, and on the predetermined relationship of the reference bodies on the implant to each other.

16. The method of claim 15, wherein the first spatial relation between the first reference body and the first end point of the bone is determined by:
  determining a fourth spatial relationship between the first reference body and a visible aspect of the first bone feature; and
  determining a fifth spatial relationship between the visible aspect of the first bone feature and a first end point of the bone model.

17. The method of claim 15, wherein at least one of the first and second 2D fluoroscopic images is generated in a direction being perpendicular to an axis of a bone shaft.

18. The method of claim 15, wherein at least one of the first and second 2D fluoroscopic images is generated in a direction being inclined to an axis of a bone shaft.

19. The method of claim 15, wherein the reference body comprises a structure forming a characteristic 2D projection image for determining a 3D orientation of the reference body.

20. The method of claim 15, further comprising the step of selecting a specific bone model from a group of bone models with different sizes and shapes, with the selected bone model corresponding to the size and shape of the fractured bone.

* * * * *